United States Patent

Curran

[11] 3,998,831
[45] Dec. 21, 1976

[54] PREPARATION OF QUINOLINE DERIVATIVES

[75] Inventor: Adrian Charles Ward Curran, Reading, England

[73] Assignee: John Wyeth & Brother Limited, Maidenhead, England

[22] Filed: July 5, 1974

[21] Appl. No.: 486,125

[30] Foreign Application Priority Data

July 12, 1973 United Kingdom ............ 33252/73

[52] U.S. Cl. ...................... 260/289 H; 260/283 SY
[51] Int. Cl.$^2$ ...................................... C07D 215/20
[58] Field of Search .... 260/283 SY, 289 D, 289 H, 260/289 R, 289 US

[56] References Cited
UNITED STATES PATENTS 1,806,564  5/1931  Prill ............................ 260/283 SY
2,608,557  8/1952  Copenhaver ................. 260/289 H

FOREIGN PATENTS OR APPLICATIONS 1,207,930  2/1956  Germany ...................... 260/289 R Primary Examiner—Richard J. Gallagher
Assistant Examiner—D. B. Springer
Attorney, Agent, or Firm—Arthur E. Wilfond; Joseph Martin Weigman

[57] ABSTRACT

A new process for preparing 5-oxo-tetrahydroquinolines comprises condensing a compound of formula II with a

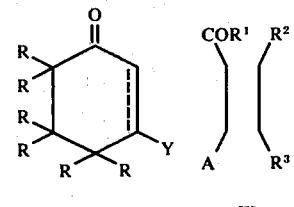

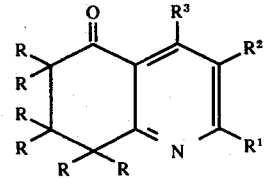

compound of formula III to obtain a compound of formula I wherein R, $R^1$, $R^2$ and $R^3$ are selected from hydrogen or alkyl, aralkyl or aryl groups, Y is $NH_2$ or OH accompanied by an ethylenic bond or Y is oxo and the double bond is absent and A is an amino or lower alkoxy group of 1–4 carbon atoms at least one of Y or A being amino. Compounds of formula I are intermediates for pharmaceuticals.

2 Claims, No Drawings

PREPARATION OF QUINOLINE DERIVATIVES

The invention relates to new processes for preparing 5-oxo-tetrahydroquinolines.

5-Oxo-tetrahydroquinolines are intermediates for the corresponding tetrahydroquinolines which themselves are useful for preparing pharmaceuticals such as those described in German Offenlegungschrift No. 2,352,585. We have now discovered a new route to 5-oxo-tetrahydroquinolines.

According to the present invention there is provided a process for preparing 5-oxo-tetrahydroquinolines of formula I

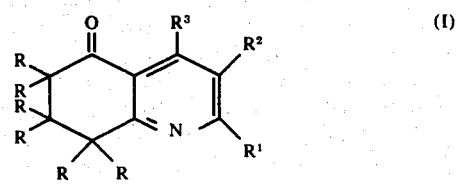

wherein R, $R^1$, $R^2$ and $R^3$ are the same or different and are selected from hydrogen, or alkyl, aralkyl or aryl groups which process comprises condensing a compound of formula II

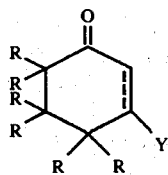

wherein R is as defined in connection with formula I and Y is $NH_2$ or OH accompanied by an ethylenic bond as shown by the dotted line or Y is oxo and the double bond is absent with a compound of formula III

wherein $R^1$, $R^2$ and $R^3$ are as defined in connection with formula I and A is an amino or a lower alkoxy group of 1 to 4 carbon atoms with the proviso that at least one of Y or A is amino. Preferably $R^3$ is hydrogen.

When any of R, $R^1$, $R^2$ or $R^3$ is an alkyl radical it is preferred that this is a lower alkyl radical which may be a straight or branched chain having from 1 to 6 carbon atoms, e.g. methyl, ethyl, n- and iso-propyl and n-, s and t-butyl. The term alkyl radical is also intended to embrace cyclic alkyl radicals e.g. cyclobutyl, cyclopentyl and cyclohexyl. When any of R, $R^1$, $R^2$ and $R^3$ is an aralkyl radical it is preferably an aryl-lower alkyl radical where the lower alkyl portion may be as discussed above for a lower alkyl radical. The aryl portion is preferably a phenyl radical.

When any of R, $R^1$, $R^2$ or $R^3$ is an aryl radical it is preferably phenyl or a substituted phenyl radical. However, other aryl radicals which may be used include naphthyl.

The preferred lower alkoxy groups for A are methoxy and ethoxy; other lower alkoxy groups which may be used are propoxy and butoxy.

The condensation of compounds of formula II and III may be achieved by heating the reactants together if desired in the presence of an anhydrous solvent, inert under the reaction conditions. Such solvents include hydrocarbon solvents with boiling points above 100° C e.g. toluene. Glacial acetic acid may also be employed but water and alcohol solvents should be avoided. The condensation may also be effected in the presence of a catalyst e.g. a weak base e.g. a tri-loweralkyl-amine such as triethylamine and a salt of a weak base and a weak acid. The weak base may be ammonia, morpholine or piperidine and the weak acid acetic acid.

Preferably $R^2$ in the above formulae is methyl and preferably $R^1$ and $R^3$ are hydrogen or $R^1$ is methyl and $R^2$ and $R^3$ are hydrogen.

The 5-oxo-tetrahydroquinolines may be converted to the corresponding tetrahydroquinolines by known methods.

The following examples illustrate the invention:

EXAMPLE 1

Preparation of 3-methyl-5,6,7,8-tetrahydroquinoline

3-Aminocyclohex-2-enone was prepared from cyclohexane-1,3-dione and ammonia by the Method of Zymakowski and Romek (Arch. Chem. 1961, 294, 759) and isolated as a pale yellow powder in 90% yield.

A mixture of 3-aminocyclohex-2-enone (11.1 g., 0.1m) and 3-ethoxy-2-methylacrolein (11.4 g, 0.1m) was heated at 120° for 16 hours in a flask equipped for downward distillation. The ethanol-water distillate (6.5 ml.) was discarded and the residual oil distilled at 0.2 mm Hg to give 3-methyl-7,8-dihydro-5(6H)quinolone as a colourless oil b.p. 78°–80° (7.8 g, 48%) which solidified on standing and was recrystallized from 40–60° petroleum ether as colourless needles m.p. 45°. Found: C, 74.81; H, 6.97; N, 8.91%. $C_{10}H_{11}NO$ requires: C, 74.51; H, 6.88; N, 8.69%.

A mixture of 3-methyl-7,8-dihydro-5(6H)-quinolone (20 g.), hydrazine hydrate (14 ml), diethylene glycol (150 ml.) and sodium hydroxide (14 g) was heated at reflux with stirring for 1 hour. The condenser was replaced by a Dean and Stark Water Separator and the heating continued for a further 3 hours. The cooled reaction mixture was diluted with water (200 ml.) and extracted with ether (3 × 150 ml.). The combined extracts were dried ($MgSO_4$) and the solvent removed in vacuo and the residual oil distilled at 15 mm Hg to give the title compound as a colourless oil b.p. 116° (17 g, 93%) G.L.C. (3% SE30, T=150°) $R_f$= 3.5 min.

EXAMPLE 2

Preparation of 3-methyl-7,8-dihydro-5(6H)-quinolone a. In Toluene

A mixture of 3-aminocyclohex-2-enone (11.1g, 0.1m) and 3-ethoxy-2-methylacrolein (11.4 g; 0.1 m) and toluene (25 ml.) were heated at reflux for 18 hours and the solvent removed in vacuo. The residual oil was dissolved in chloroform (50 ml.) and washed with 2N HCl (3 × 10 ml.). The combined washings were adjusted to pH 9.0 with sodium carbonate then extracted with chloroform (3 × 20 ml.) and the combined extracts dried. The solvent was removed in vacuo. The residual oil was distilled to give the title compound as a colourless crystalline solid b.p. 78°–80°/0.2 mm Hg (7.6 g, 48%).

b. In Glacial Acetic Acid

A mixture of 3-aminocyclohex-2-enone (24.1g, 0.22m) and 3-ethoxy-2-methylacrolein (27.7g, 0.24m) in glacial acetic acid (55 ml.) was heated at reflux for 24 hours, cooled to 0° C and filtered. The solid (5g.) was recrystallised from ethanol as colourless needles m.p. 253° and identified di(2-methylprop-2-enalyl)amine.
Found: C, 62.5; H, 7.5; N, 9.2:. $C_8H_{11}NO_2$ requires; C, 62.7; H, 7.2; N, 9.2%.

The acetic acid soluble material was evaporated in vacuo and the residual oil dissolved in chloroform (25 ml.) and washed with 2N HCl (3 × 15 ml.) and the combined washings adjusted to pH 9.0 with $Na_2CO_3$ and extracted with chloroform (3 × 50 ml.). The combined extracts were dried, evaporated in vacuo and the residual oil distilled at 0.2 mm Hg to give the title compound as a colourless crystalline solid (13.5g. 40%) b.p. 78°–80°.

EXAMPLE 3

Preparation of 3-methyl-7,8-dihydro-5(6H)-quinolone

A mixture of cyclohexane-1,3-dione (11.2 g. 0.1 m), 3-amino-2-methylacrolein (8.5 g. 0.1m) triethylamine (5 ml.) and ammonium acetate (100 mg) were heated with stirring at 120° in an oil bath for 12 hours. The cooled reaction mixture was diluted with ether (50 ml.) and the solution washed with 2N HCl (3 × 15 ml.) The combined washings were adjusted to pH 9.0 with sodium carbonate and extracted with ether (3 × 50 ml.) The combined extracts were dried, evaporated in vacuo and the residual oil distilled at 0.2 mm Hg to give the title compound as a colourless crystalline solid b.p. 80° (7.5 g. 48%).

EXAMPLE 4

Preparation of 3-methyl-7,8-dihydro-5(6H)-quinolone

A mixture of 3-aminocyclohex-2-enone (11.1 g. 0.1m) and 3-amino-2-methylacrolein (8.5 g. 0.1 m) in toluene (15 ml.) was heated at reflux below a Dean and Stark water separator for 48 hours. The solvent was removed and the residual oil distilled at 0.2 mm Hg to give the title compound as a colourless crystalline solid (0.5 g, 4%).

EXAMPLE 5

Preparation of 3-methyl-7,8-dihydro-5(6H)-quinolone

A mixture of cyclohexane-1,3-dione (22.4 g., 0.2 mol.), 3-amino-2-methylacrolein (17 g., 0.2 mol.), triethylamine (10 ml.) and piperidinium acetate (0.25 g.) was heated with stirring in an oil bath at 120° C for 24 hours. The cooled reaction mixture was dissolved in 2N HCl (50 ml.) and extracted with ethyl acetate (3 × 50 ml.) and the organic extracts discarded. The aqueous solution was adjusted to pH 10 with sodium carbonate and extracted with chloroform (3 × 50 ml.). The combined extracts were dried ($MgSO_4$) and the solvent removed in vacuo. The residual oil was distilled to give the title compound as a colourless oil (17 g., 52%) b.p. 79°/0.2 mm Hg which solidified.

EXAMPLE 6

Preparation of 3,7,7-trimethyl-7,8-dihydro-5(6H)-quinolone

A mixture of 3-amino-2-methylacrolein (8.5 g., 0.1 mol.) and dimedone (14 g., 0.1 mol.) was treated with triethylamine (5 ml.) and ammonium acetate (0.1 g.) and heated in an oil bath at 120° C with stirring for 20 hours. The cooled reaction mixture was diluted with 2N HCl (50 ml.) and extracted with ethyl acetate (2 × 50 ml.) and the extracts discarded. The aqueous solution was adjusted to pH 10.0 with sodium carbonate and extracted with ethyl acetate (3 × 50 ml.). The combined extracts were dried ($MgSO_4$ and the solvent removed to give a residual oil which was distilled to give the title compound as a colourless oil (7.8 g., 40%) b.p. 80°/0.2 mm Hg. ($R_T$ = 2 min. 2% OV17, T=150°).

The free base was dissolved in ether and the solution treated with an excess of ethereal hydrogen chloride and the resultant solid removed by filtration, recrystallised from isopropanol to give the hydrochloride of the title compound as colourless needles m.p. 232°–5°. (Found: C, 63.8; H, 7.1; N, 6.1. $C_{12}H_{15}NO.HCl$ requires: C, 63.8; H, 7.1: N, 6.2%).

EXAMPLE 7

Preparation of 3,7,7-Trimethyl-7,8-dihydro-5(6H)-quinolone

A mixture of 3-amino-5,5-dimethylcyclohex-2-enone (27.8g., 0.2 mol.) and 2-methyl-3-ethoxyacrolein (22.8 g., 0.2 mol.), in an apparatus equipped for downward distillation, was heated in an oil bath at 120° until the theoretical quantity of distillate was collected (13 ml.) The cooled residue was diluted with 2N HCl (50 ml.), extracted with ethyl acetate (3 × 50 ml.) and the combined extracts discarded. The aqueous solution was adjusted to pH 9.0 with sodium carbonate and extracted with ethyl acetate (3 × 50 ml.). The combined extracts were dried ($MgSO_4$) and the solvent removed in vacuo and the residual oil distilled to give the title compound as a colourless oil (23 g., 53%) b.p. 83°/0.2 mm Hg. ($R_T$ = 2 min., 2% OV17, T=150° C).

EXAMPLE 8

Preparation of 2-Methyl-7,8-dihydro-5(6H)-quinolone

A mixture of 3-aminocyclohex-2-enone (22 g., 0.2 mol.) and 4-methoxybut-3-en-2-one (20.0 g., 0.2 mol), in an apparatus equipped for downward distillation, was heated in an oil bath at 120° C until the theoretical amount of distillate had been collected (13 ml.). The cooled residue was dissolved in 2N HCl (50 ml.) and extracted with ethyl acetate (3 × 50 ml.) and the combined extracts discarded. The aqueous solution was adjusted to pH 9.0 with sodium carbonate and extracted with chloroform (3 × 50 ml.). The combined extracts were dried ($MgSO_4$) and the solvent removed in vacuo and the residual oil distilled to give the title compound (22.5 g., 72%) b.p. 72°–6°/0.1 mm Hg. The free base was dissolved in ether and treated with an excess of ethereal hydrogen chloride. The resultant solid was isolated and recrystallised from isopropanol to give the hydrochloride of the title compound as colourless needles m.p. 225° C. (Found: C, 60.9; H, 6.3; N, 6.99. $C_{10}H_{11}NO.HCl$ requires: C, 60.7; H, 6.1; N, 7.1%).

EXAMPLE 9

Preparation of 2-methyl-7,8-dihydro-5(6H)-quinolone

A mixture of cyclohexane-1,3-dione (11.2 g., 0.1 mol.) and 4-aminobut-3-en-2-one (8.5 g., 0.1 mol.) was heated at 120° C, in a flask equipped for downward distillation, until the theoretical amount of water (3.6 ml.) had been obtained. The cooled reaction mixture was diluted with 2N HCl (50 ml.) and extracted with ethyl acetate (3 × 50 ml.). The aqueous phase was adjusted to pH 10.0 with sodium carbonate and extracted with ethy accetate (3 × 50 ml.). The combined extracts were dried (MgSO₄) and the solvent removed in vacuo and the residual oil distilled to give the title compound (11 g., 68%). b.p. 65°/0.05 mm Hg. The base was dissolved in ether and treated with an excess of ethereal hydrogen chloride and the resultant solid recrystallised from isopropanol to give the hydrochloride of the title compound as colourless needles. m.p. 223° C. (Found: C, 60.7; H, 6.3; N, 6.8. C10H11NO.HCl requires: C, 60.7; H, 6.1; N, 7.1:).

I claim:
1. A process for preparing a 5-oxotetrahydroquinoline of formula

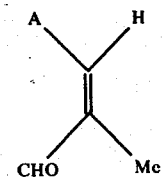

where R is independently selected from hydrogen and methyl, which process comprises the step of heating in toluene or glacial acetic acid a compound of formula

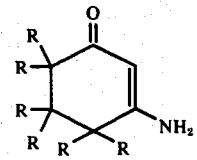

where R is as defined above, with a compound of formula

A\_H
||
CHO  Me where A is a lower alkoxy of 1 to 4 carbon atoms.
2. A process as claimed in claim 1 wherein A is methoxy or ethoxy.

* * * * *